United States Patent
Nadarajah et al.

(10) Patent No.: US 9,542,530 B2
(45) Date of Patent: Jan. 10, 2017

(54) SYSTEM AND METHOD FOR MULTI-DIMENSIONAL PROFILING OF HEALTHCARE PROFESSIONALS

(71) Applicant: IMS Health Incorporated, Danbury, CT (US)

(72) Inventors: Sivakumar Nadarajah, Bridgewater, NJ (US); Sanmugam Aravinthan, Lake Hiawatha, NJ (US)

(73) Assignee: IMS Health Incorporated, Danbury, CT (US)

( * ) Notice: Subject to any disclaimer, the term of this patent is extended or adjusted under 35 U.S.C. 154(b) by 459 days.

(21) Appl. No.: 14/059,083

(22) Filed: Oct. 21, 2013

(65) Prior Publication Data
US 2015/0113002 A1    Apr. 23, 2015

(51) Int. Cl.
*G06F 17/30* (2006.01)
*G06F 19/00* (2011.01)

(52) U.S. Cl.
CPC ......... *G06F 19/327* (2013.01); *G06F 17/3053* (2013.01); *G06F 17/30864* (2013.01); *G06F 17/30867* (2013.01)

(58) Field of Classification Search
CPC ............ G06F 17/3053; G06F 17/30864; G06F 17/30867
USPC ........................................................ 707/748
See application file for complete search history.

(56) References Cited

U.S. PATENT DOCUMENTS

| | | | |
|---|---|---|---|
| 8,515,777 B1* | 8/2013 | Rajasenan | G06Q 50/22 705/2 |
| 2012/0060216 A1* | 3/2012 | Chaudhri | G06F 19/322 726/21 |
| 2012/0208634 A1* | 8/2012 | Cohen | G06F 19/322 463/29 |
| 2012/0239417 A1* | 9/2012 | Pourfallah | G06Q 10/00 705/2 |
| 2013/0096991 A1* | 4/2013 | Gardner | G06Q 30/0623 705/7.42 |
| 2013/0124523 A1* | 5/2013 | Rogers | G06F 19/32 707/737 |
| 2014/0243635 A1* | 8/2014 | Arefieg | A61B 5/157 600/365 |

* cited by examiner

*Primary Examiner* — Mark E Hershley
(74) *Attorney, Agent, or Firm* — Fish & Richardson P.C.

(57) ABSTRACT

The disclosure generally describes computer-implemented methods, software, and systems for ranking healthcare professionals, including: receiving healthcare information submitted by a user; launching search delegators to search respective channels of social media based on the healthcare information; receiving meta search records from the search delegators; scoring the meta search records based on the healthcare information as well as the channel of social media where the meta search record was found; filtering the meta search records based on the corresponding scores; and providing the filtered meta search records to the user.

19 Claims, 8 Drawing Sheets

| Parameter | Baseline Score | Mandatory in Search Parameter | Score Configurable? |
|---|---|---|---|
| First Name | 1 | Yes | Yes |
| Last Name | 1 | Yes | Yes |
| Specialty | 3 | No | Yes |
| Workplace | Tokenized. Entity names get a score of 1 (blog and news only). For others workplace can be validated | No | Yes |
| Title, Degree | 0 | Yes | Yes |
| City | 0 | No | Yes |
| State | 0 | No | Yes |
| Street Address | 0 | No | Yes |

| Content Type | High Confidence Score | Workplace validatable? |
|---|---|---|
| Blog | 6 and above | No |
| Youtube | 5 and above | Yes |
| LinkedIn | 5 and above | Yes |
| Facebook | 5 and above | Yes |
| Twitter | 5 and above | Yes |
| News | 6 and above | No |

SYSTEM AND METHOD FOR MULTI-DIMENSIONAL PROFILING OF HEALTHCARE PROFESSIONALS

BACKGROUND

Healthcare professionals, such as medical doctors, nurses, and physical therapists, are generally associated with publications.

OVERVIEW

In one aspect, some implementations provide method for ranking healthcare professionals. The method includes receiving healthcare information submitted by a user; launching search delegators to search respective channels of social media based on the healthcare information; receiving meta search records from the search delegators; scoring the meta search records based on the healthcare information as well as the channel of social media where the meta search record was found; filtering the meta search records based on the corresponding scores; and providing the filtered meta search records to the user.

Implementations may include one or more of the following features. In one configuration, scoring the meta search records may include ranking the meta search records according to (i) a match index indicating a degree of relatedness between the particular search record and the submitted healthcare information, and (ii) an authoritative index indicating a level of trustworthiness of the channel of social media where the particular search record was found by the corresponding search delegator. Ranking the meta search records according to the match index further comprises: semantic processing of the meta search records by: (i) tokenizing the particular meta search records into tokens; (ii) scoring each token based on the match index; and (iii) aggregating scores of the tokens for the particular meta search record. The semantic processing may include applying an ontology to analyze the meta search records. The semantic processing may additionally include: revising the ontology based on the analyzed meta search records, the revised ontology providing an improved aggregated score for the analyzed meta search records.

In another configuration, filtering may further include: removing meta records with corresponding scores under a cut-off threshold. In yet another configuration, the method may further include providing an interface to the user for the user to classify contents of the filtered meta data records as positive, negative or neutral.

In still another configuration, receiving healthcare information may include receiving information capable of identifying a healthcare provider. In particular, healthcare information may be received in the form of information identifying a specialty of healthcare providers. Scoring the meta search records may include categorizing the meta search records into a first category of data generated by the healthcare provider and a second category of data generated by others mentioning the healthcare provider. Scoring the meta search records may further include: identifying a professional interest of the healthcare provider based on the first category of data. Scoring the meta search records may include analyzing the second category of data to determine whether the first category of data is correlated with the second category of data. In response to determining that the first category of data is correlated with the second category of data, establishing a digital profile of the healthcare provider based on (i) the identified professional interest of the healthcare provider; and (ii) the first category of data of the healthcare provider correlated with the second category of data of the healthcare provider; and integrating the digital profile into a database for the user that includes digital profiles of more than one healthcare providers. Scoring the meta search records comprises analyzing the second category of data to determine an influence of the healthcare provider. The method may additionally include: establishing a digital profile of the healthcare provider based on (i) the identified professional interest of the healthcare provider; and (ii) the influence of the healthcare provide as determined by analyzing the second category of data of the healthcare provider; and integrating the digital profile into a database for the user that includes digital profiles of more than one healthcare providers. Scoring the meta search records may additionally include: determining whether a particular meta search record is corroborated by data from non-social media regarding the healthcare provider. Scoring the meta search records may further include: in response to determining that the particular meta search record is corroborated by data from non-social media, increasing the score of the particular meta search record. Scoring the meta search records may further include: in response to determining that the particular search record is not corroborated by data from non-social media, attenuating the score for the particular search record.

In another aspect, some implementations provide a computer system, including at least one processor, wherein the at least one processor is configured to perform the operations of: receiving healthcare information submitted by a user; launching search delegators to search respective channels of social media in response to the healthcare information; receiving meta search records from the search delegators; scoring the meta search records based on the healthcare information as well as the channel of social media where the meta search record was found; filtering the meta search records based on the corresponding scores; and providing the filtered meta search records to the user.

Implementations may include one or more of the following features. In one configuration, the operation of scoring the meta search records may include ranking the meta search records according to (i) a match index indicating a degree of relatedness between the particular search record and the submitted healthcare information, and (ii) an authoritative index indicating a level of trustworthiness of the channel of social media where the particular search record was found by the corresponding search delegator. In another configuration, the operation of ranking the meta search records according to the match index may further include: semantic processing of the meta search records by: (i) tokenizing the particular meta search records into tokens; (ii) scoring each token based on the match index; and (iii) aggregating scores of the tokens for the particular meta search record. The semantic processing may include: applying an ontology to analyze the meta search records. The semantic processing may further include: revising the ontology based on the analyzed meta search records, the revised ontology providing an improved aggregated score for the analyzed meta search records.

The operation of filtering may further include: removing meta records with corresponding scores under a cut-off threshold. The operations may further include: providing an interface to the user for the user to classify contents of the filtered meta data records as positive, negative or neutral.

Healthcare information may include information capable of identifying a healthcare provider. Healthcare information may also include information identifying a specialty of healthcare providers.

Scoring the meta search records may include categorizing the meta search records into a first category of data generated by the healthcare provider and a second category of data generated by others mentioning the healthcare provider. Scoring the meta search records may further include: identifying a professional interest of the healthcare provider based on the first category of data.

Scoring the meta search records may include analyzing the second category of data to determine whether the first category of data is correlated with the second category of data. The operations may further include: in response to determining that the first category of data is correlated with the second category of data, establishing a digital profile of the healthcare provider based on (i) the identified professional interest of the healthcare provider; and (ii) the first category of data of the healthcare provider correlated with the second category of data of the healthcare provider; and integrating the digital profile into a database for the user that includes digital profiles of more than one healthcare providers. Scoring the meta search records may include analyzing the second category of data to determine an influence of the healthcare provider. The operations may further include: establishing a digital profile of the healthcare provider based on (i) the identified professional interest of the healthcare provider; and (ii) the influence of the healthcare provide as determined by analyzing the second category of data of the healthcare provider; and integrating the digital profile into a database for the user that includes digital profiles of more than one healthcare providers. Scoring the meta search records may additionally include: determining whether a particular meta search record is corroborated by data from non-social media regarding the healthcare provider. Scoring the meta search records may additionally include: in response to determining that the particular meta search record is corroborated by data from non-social media, increase the score of the particular meta search record. Scoring the meta search records may additionally include: in response to determining that the particular search record is not corroborated by data by non-social media, attenuate the score for the particular search record.

In still another aspect, some implementations may provide a computer-readable medium comprising software instructions that, when executed by a computer, causes the computer to perform the operations of: receiving healthcare information submitted by a user; launching search delegators to search respective channels of social media in response to the healthcare information; receiving meta search records from the search delegators; scoring the meta search records based on the healthcare information as well as the channel of social media where the meta search record was found; filtering the meta search records based on the corresponding scores; and providing the filtered meta search records to the user.

Implementations of the above techniques include a method, computer program product and a system. The computer program product is suitably embodied in a non-transitory machine-readable medium and includes instructions executable by one or more processors. The instructions are configured to cause the one or more processors to perform the above described actions.

The system includes one or more processors and instructions embedded in a non-transitory machine-readable medium that are executable by the one or more processors. The instructions, when executed, are configured to cause the one or more processors to perform the above described actions. The default position is not to use any external databases, but the system could be configured to perform a database check if needed.

The details of one or more aspects of the subject matter described in this specification are set forth in the accompanying drawings and the description below. Other features, aspects, and advantages of the subject matter will become apparent from the description, the drawings, and the claims.

DETAILED DESCRIPTION

This disclosure generally describes systems and methods for profiling healthcare professionals in an automatic fashion. Healthcare professionals, like medical doctors, may leave a trail of publicly available data about their professional activities. The publicly available data may include traditional data sources such as board record, clinical trial record, journal publication record, etc. The publicly available data may also include social media data that became available more recently. Some implementations disclosed herein may automatically gather social media data about a healthcare professional from multiple social media channels. The automatically gathered social media data may be known as meta search records and may come from various social media channels. Meta search records from a particular social media channel may be scored according to a matching quality between the meta search record and the healthcare information submitted by the user. The scoring may also factor in the authoritativeness of the particular social media channel where the meta search record was identified. Aggregated score for meta search records from a particular social media channel may be based on tokenization of the collected social media data. Social media data from various channels may be correlated against each other to establish a digital profile of the particular healthcare professional. Social media data may include publications made by the healthcare professional himself. Social media data may also include publications by others mentioning the healthcare professional. Social media data in the latter category may be evaluated to establish an influence factor indicating the ability of the healthcare professional as an opinion leader. Moreover, the social media data may be corroborated against more traditional data sources such as board record, clinical trial record, journal publication record, etc. For example, the meta search record that has been corroborated with more traditional data may receive increased score while the score for a meta search record that cannot be corroborated against traditional data sources may be attenuated. The scored meta search records may be ranked and then filtered, for example, according to a threshold level. The meta search records with scores above the threshold level may be presented to a user for further review.

Figure 1:
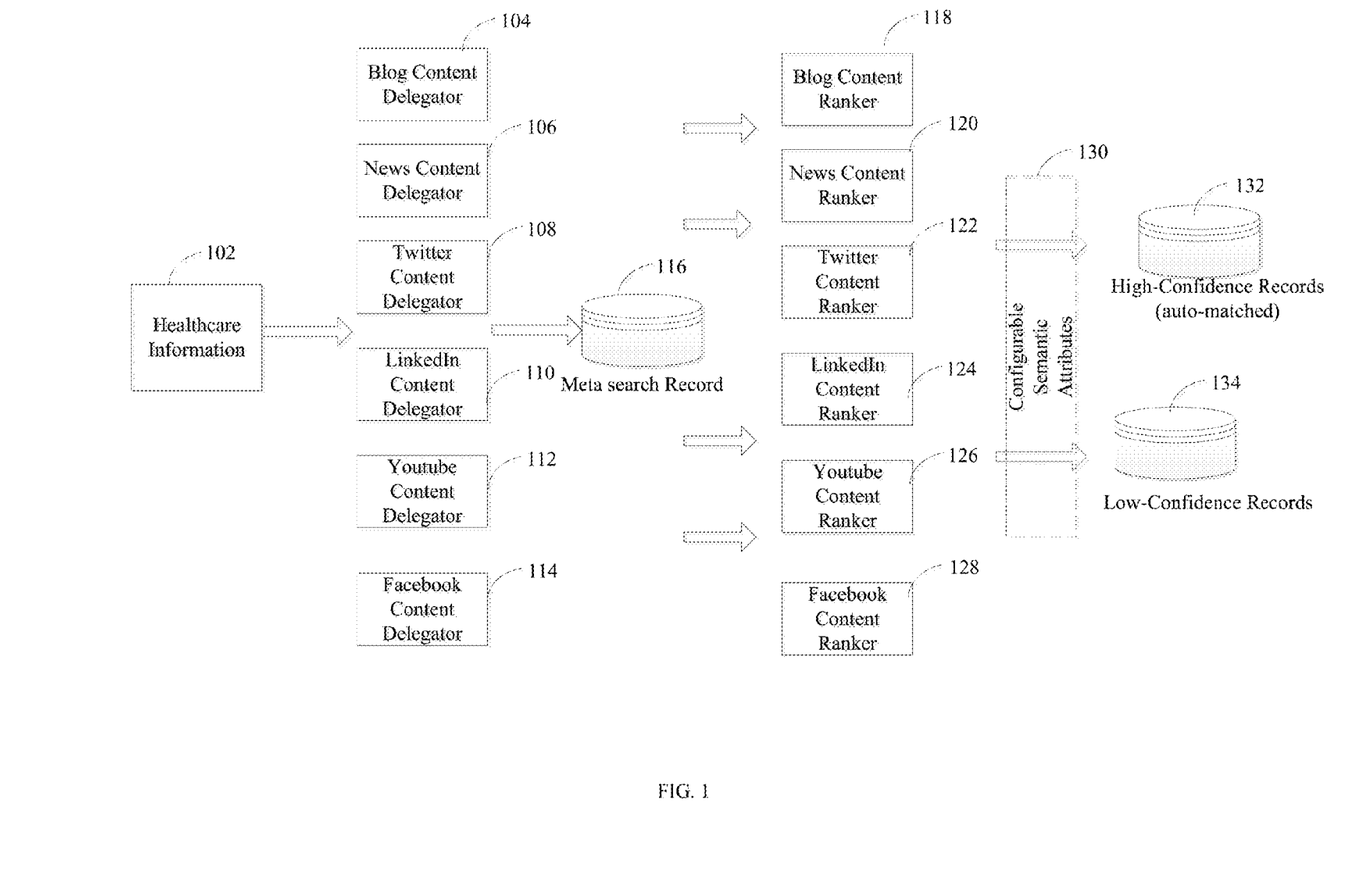
FIG. 1 is a diagram showing a system-level work-flow for multi-dimensional profiling of a healthcare professional according to some implementations.

FIG. 1 is a diagram showing a system-level work-flow for multi-dimensional profiling of a healthcare professional according to some implementations. Healthcare information 102 may be received in various forms from a human user. Healthcare information 102 may be received in the form of information that may be used to identify a particular healthcare professional, for example, first name, last name, hospital affiliation, specialty, alma mater, etc. Healthcare information 102 may also include a general description of a specialty, such as, for example, cardiology, neurology, interventional radiology, etc.

In response to healthcare information 102, search delegators may be launched to comb various social media channels for information related to healthcare information 102. The related information may include, for example, postings by a healthcare professional on a topic in the particular specialty, the healthcare professional's LinkedIn updates, comments made by other healthcare professional such as endorsements at LinkedIn or comments by colleagues at work, during collaboration, at a conference or convention, etc. In some implementations, healthcare information 102 may be generated automatically in anticipation of prior submissions by human users. For example, in one configuration, after receiving a user submission of "radiology," search delegators may be launched proactively to search for information regarding sub-specialties of radiology, including, for example, diagnostic radiology, interventional radiology, etc. In some implementations, crawlers or spiders may be implemented to facilitate proactive searches. The crawlers and spiders may be adapted to the specific application interfaces of the respective social media channels.

A search delegator may include a thread or a pool of threads targeting a particular social media channel. The threads may be launched asynchronously, without having to wait for the return status of each thread. The threads may also be launched synchronously, in which the master thread may wait for the return status for each slave thread. As illustrated by FIG. 1, search delegators may be launched to target a variety of social media channels. Example search delegators may include, but are not limited to, blog content delegator 104, news content delegator 106, twitter content delegator 108, LinkedIn content delegator 110, YouTube content delegator 112, Facebook content delegator 114, etc. The social media channel may evolve as more and more social media channels are developed, matured, merged etc.

The search delegators may return meta search record 116 from each social media channel. Meta search record 116 may generally include information matching the submitted healthcare information. The match may include verbatim textual match. The match may also include textual approximation, for example, when acronyms are involved in the matching process.

Meta search record 116 from each social media channel may be scored and ranked in accordance with the descriptions herein. In some implementations, the scoring and ranking may be performed per social media channel. As illustrated in FIG. 1, the ranking may be performed by blog content ranker 118, news content ranker 120, twitter content ranker 122, LinkedIn content ranker 124, YouTube content ranker 126, Facebook content ranker 128. Each ranker may be implemented as a thread. In one configuration, each thread may spawn a new thread when contents of the social media channel are updated. For example, when news feed has been updated, a news content ranker thread may spawn a new instance of thread to score and rank the updated content.

In some implementations, ranked contents may be filtered according to configurable semantic attributes 130. The configurable semantic attribute 130 may be adapted to zero in on topics being mentioned more frequently. In one configuration, the semantic attribute may be configured to detect a changing trend of topics being mentioned, for example, from one specialty to another, for a particular healthcare professional. In another configuration, the semantic attribute may be configured to sense a popularity of the particular healthcare professional in a specialty. For example, whether the on-line postings of the particular healthcare professional can generate substantive feedback from a community of fellow healthcare professionals, especially when the on-line postings of the particular healthcare professional can generate substantial feedback in a substantive way from the community. In yet another configuration, the semantic attribute may be configured to detect a tone for community feedback regarding postings of a particular healthcare professional. For example, the semantic attributes may be configured to detect whether the community feedback conveys a sense of endorsement, appreciation, skepticism, or dismissal. The characterization of community feedback may facilitate a better characterization of a particular healthcare professional in a given specialty at the particular moment, for example, the ability of the healthcare professional to influence the community of fellow healthcare professionals in a given specialty. Moreover, in one configuration, the semantic attributes may be configured to detect whether the contents of published comments about the healthcare professional can be characterized as positive or negative. For example, the semantic attributes may be configured to determine whether the healthcare professional receives overwhelmingly or substantially positive comments on places like yelp or google+. Similarly, the semantic attributes may be configured to sense whether the healthcare professional is participating in healthcare discussions, for example, in an academic debate whether COX-2 drugs may or may not be efficacious for treating cancer. Additionally, the semantic attributes may be configured to infer whether the healthcare professional may be involved in malpractice suits, investigations at the medical board, regulatory agencies (such as, for example, the federal trade commission for alleged bribery, kick-back, or anti-trust investigations), or complaints at the better business bureau, etc.

Thereafter, the filtered ranked meta search record may be classified as either high-confidence records 132 or low-confidence records 134. The classification may be implemented as a threshold comparison. For example, if a filtered ranked meta search record is above a threshold value, then the filtered ranked meta search record is classified as a high-confidence record. If, however, the filtered ranked meta search record is not above the threshold value, then the filtered ranked meta search record is classified as a low-confidence record. In some implementations, the high-confidence records 132 may be presented automatically to the user submitting the healthcare information for further review. The low-confidence records 134 may be ignored.

Figure 2:
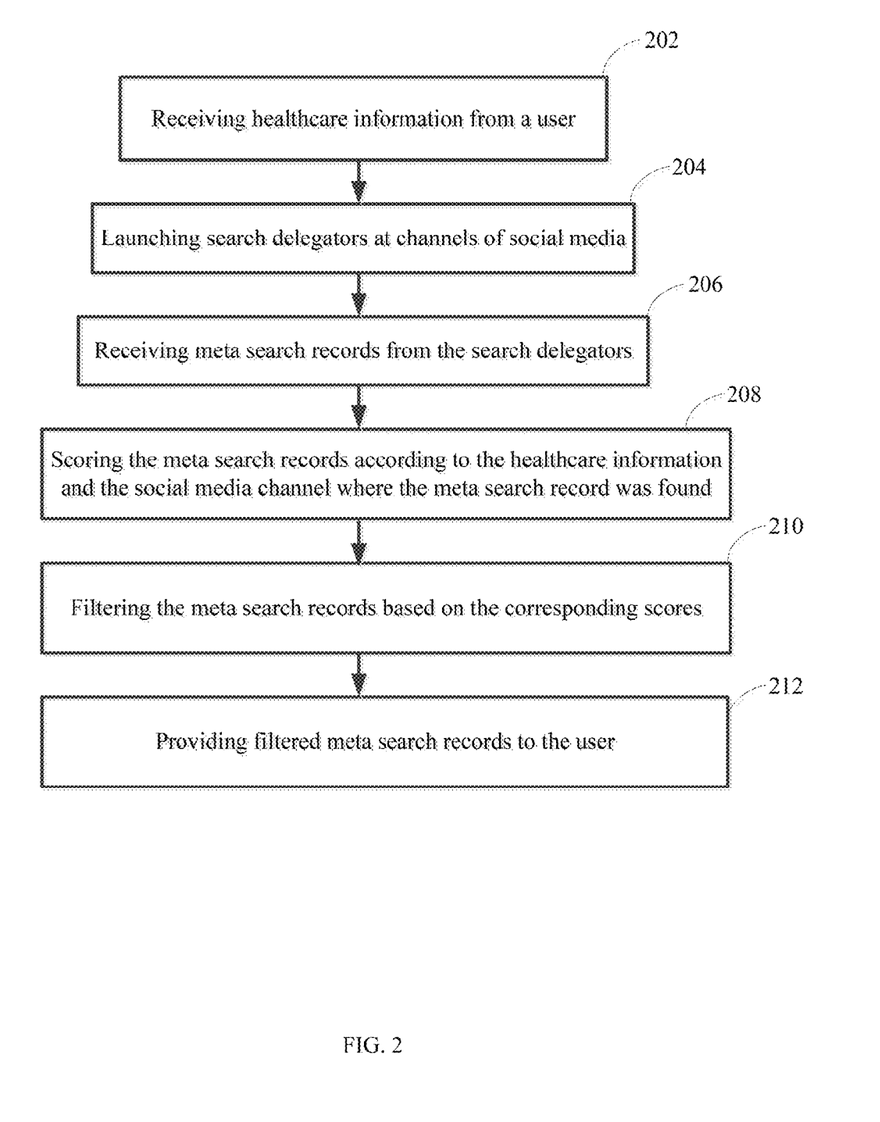
FIG. 2 is a flow chart for profiling healthcare professionals according to some implementations.

FIG. 2 is a flow chart for profiling healthcare professionals according to some implementations. Initially, healthcare information may be received from a user. As described herein, healthcare information 102 may provide the seed information, for example, information capable of identifying a healthcare professional (such as a practicing doctor, a treating physical therapist, etc.). The seed information may include a specialty such as a therapeutic area. For example, seed information may include: metabolic disorder, adrenaline deficit, diabetes, etc. In some implementations, a user may submit healthcare information 102 to identify opinion leaders in a specialty area, such as, for example, type II diabetes. Similarly, a user may submit healthcare information to identify healthcare professionals who had furnished significantly above average prescriptions of a particular drug or device. For example, for those doctors who had prescribed Vioxx for treating rheumatoid arthritis before the product withdrawal by the manufacturer, these doctors may need a substitute prescription drug. Likewise, a user may submit healthcare information identifying a local interventional cardiologist. The search, however, may provide the user with opinion leaders on the national level in the same specialty of interventional cardiology.

In response to healthcare information 102, search delegators may be launched at various social media channels (204). As described herein, the social media channels may include any existing or yet to be developed social media conduits. Example social media channels may include, but are not limited to, blogs, news feeds, twitters, Weibo, LinkedIn, Facebook, Youtube, etc. By way of example and not limitation, a search delegator targeting Youtube may be coupled to a transcription (or voice recognition) engine to allow text mining of the content. The search delegator may additionally include a speaker recognition plug-in or module to locate the portion of the speech made by a particular healthcare professional. The speech contents of others during the Youtube media may still be transcribed and analyzed to determine, for example, feedback to the healthcare professional's speech. Comments following the Youtube media posting may be textually analyzed in a similar fashion to determine feedback from the audience.

Moreover, the contents at the social media web-sties may be refreshed in real-time. In response, the search delegators may monitor the updates in an incremental fashion. For example, the search delegator targeting a particular social networking channel may restrict the search to the contents that have been updated since the search delegator searched the particular social networking channel last time. As disclosed herein, each search delegator may include a master thread in existence at launch. The master thread may spawn slave threads periodically or in response to accumulated updates in the social media channel being searched.

Search results may be returned from the launched search delegators. The search results may be received in the form of meta search record (206). In one configuration, a meta search record may be structured as indexed data, instead of the source posing (where the meta search record was identified) verbatim. A meta search record may also include a nested indexing structure to for hierarchical matching at various levels. An example nested index may be: metabolic disorder→cardiovascular disease→hypertension→stage I hypertension. A meta search record may include matching words at each level. As disclosed herein, a matching word may include an exact match, letter for letter. A matching word may also include a literal match, for example, full spelling of an acronym, acronym of a full spelling, alternate acronyms, interchangeable words, etc. In some implementations, a linguistic dictionary or database may be maintained for words to be treated as literal matches. The research results may also arrive in a compressed form, for example, as a digest or abstract, with the full content available for downloading later. The digest or abstract may follow the indexed structure as noted above.

Subsequently, the received meta search records may be scored and ranked to triage the most promising leads for further consideration. In some implementations, scoring a meta search record may be performed according to the healthcare information 102 and the social media channel from which the meta search record was initially found. In some implementations, a matching index and an authoritative index may be used in the scoring process. The matching index may quantify a degree of match between the meta search record and the healthcare information 102. For example, when the user submits healthcare information regarding a particular healthcare condition, or information identifying a healthcare professional whose practice area includes the particular healthcare condition, a matching index may be computed to indicate to what extent the meta search record matches the submitted healthcare information.

Figure 3A:
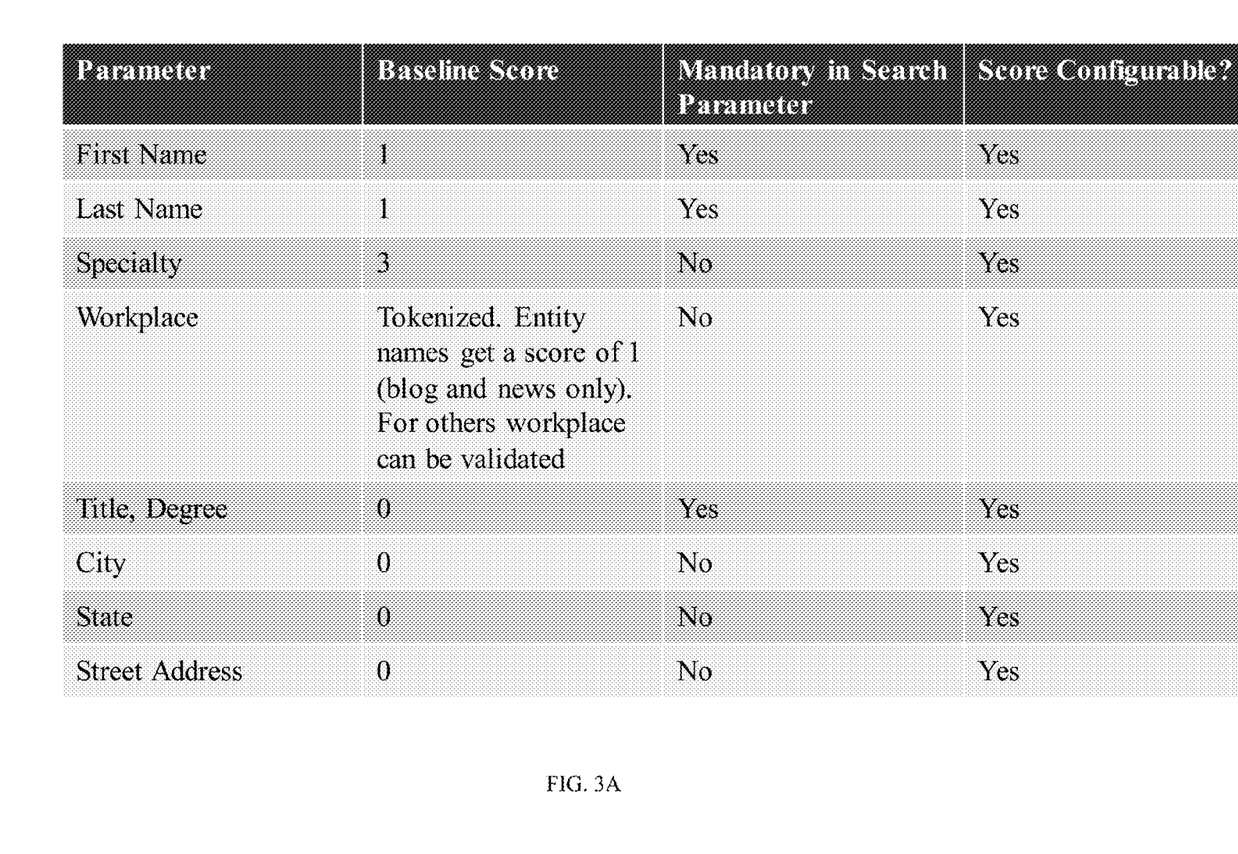
FIG. 3A is a flow chart for ranking meta search record according to some implementations.

Referring to FIG. 3A, which shows example matching scores according to some implementations, a matched first or last name may correspond to one point. In one configuration, for example, when the submitted healthcare information identifies a particular healthcare professional, the first name and last name may be mandatory as search parameters to be matched. A mandatory parameter means a matching parameter may not be missing in the meta search record. As described herein, the matching score is configurable. For example, all things being equal, a matching first name may score more than a matching last name in one configuration. Similarly, matching names with different spellings may be configured. For example, William and Bill, Richard and Dick, Alexandria and Sasha, etc. Similarly, Wang, Wong, and Ong could be the same last name and may be configured accordingly as matching last names.

As illustrated by FIG. 3A, a matching specialty may earn a score of three points. As described herein, the matching specialty may include alternate spellings, for example, acronyms. The age mobile computing and cloud computing has seen on-line users publishing comments from a variety of mobile devices. The space for inputting texts on these mobile devices may be more restricted than a traditional keyboard. On-line users may enter comments from a plethora of locations. The published texts may not be as organized as would be the case for a traditional keyboard. As a result, the matching may accommodate situations in which on-line users use abbreviated or simplified terms. For example, CV, cardio, card-vas, could all mean cardiovascular at a particular social media channel. The alternative spellings may be configured to fine-tune the sensitivity of the matching index. In one configuration, a matching specialty may not be mandatory.

As illustrated by FIG. 3A, other parameters with a matching score may include workplace, title/degree, city, state, and street address. As disclosed herein, a parameter may be configured as either mandatory or non-mandatory. The baseline score for each parameter may be configured. In one configuration, the score attributions to title/degree, city, state, street address may be zero. A matching work-place, however, may earn some points. In particular, a workplace term may be segmented into more than one token. Each token may represent a particular phrase, as a minimally meaningful text unit for searching purposes. Tokenization may represent a divide-and-conquer approach through which unstructured data, such as a long string or work history, may be scored at component levels to more fairly characterize the matching as a whole.

Figure 3B:
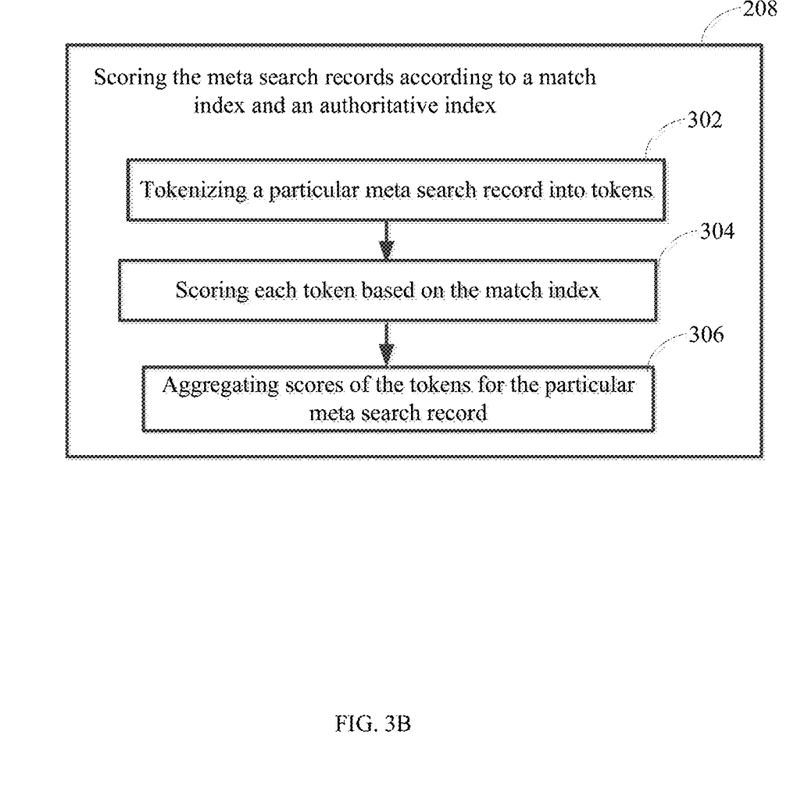
FIG. 3B shows an example matching index according to some implementations.

Referring to FIG. 3B, a flow chart for scoring a meta search record according to some implementations, a particular meta search record may be tokenized into tokens (302). Tokenization may remove punctuations that separate words in a sentence. However, tokenization may not remove, for example, apostrophes in a surname such as O'Neill. Moreover, white spaces within names (for example, San Francisco. Los Angeles) may not be removed. Similarly, white spaces within borrowed foreign phrases (for example, et al., au fait) may not be removed. In particular, tokenization may be language dependent. Thus, tokenization may include a language detection module to determine the language of an underlying comment. For postings that include more than one language, determining the language may be performed segment by segment.

By way of example and not limitation, "Bay Street Medical Center" may be tokenized into two tokens, namely, "Bay Street" and "Medical Center." Each token may be matched individually (304). The individual match may be verbatim or literal (including alternative spellings). Each token may then be scored on a matching index. Using the same example above, matching "Bay Street" may lead to a score of three points, while matching "Medical Center" may score another two points. As hospitals may have alternate names, such as hospital, health science center, medical center, a literal match may be more suited. Moreover, hospitals may be merged or spun off over the years. A chronicle database may be maintained to smooth the matching process by factoring in the naming history of a particular entity. The scored matching index from each token may be aggregated for a particular meta search record to derive a combined score for the matching index (306).

Figure 3C:
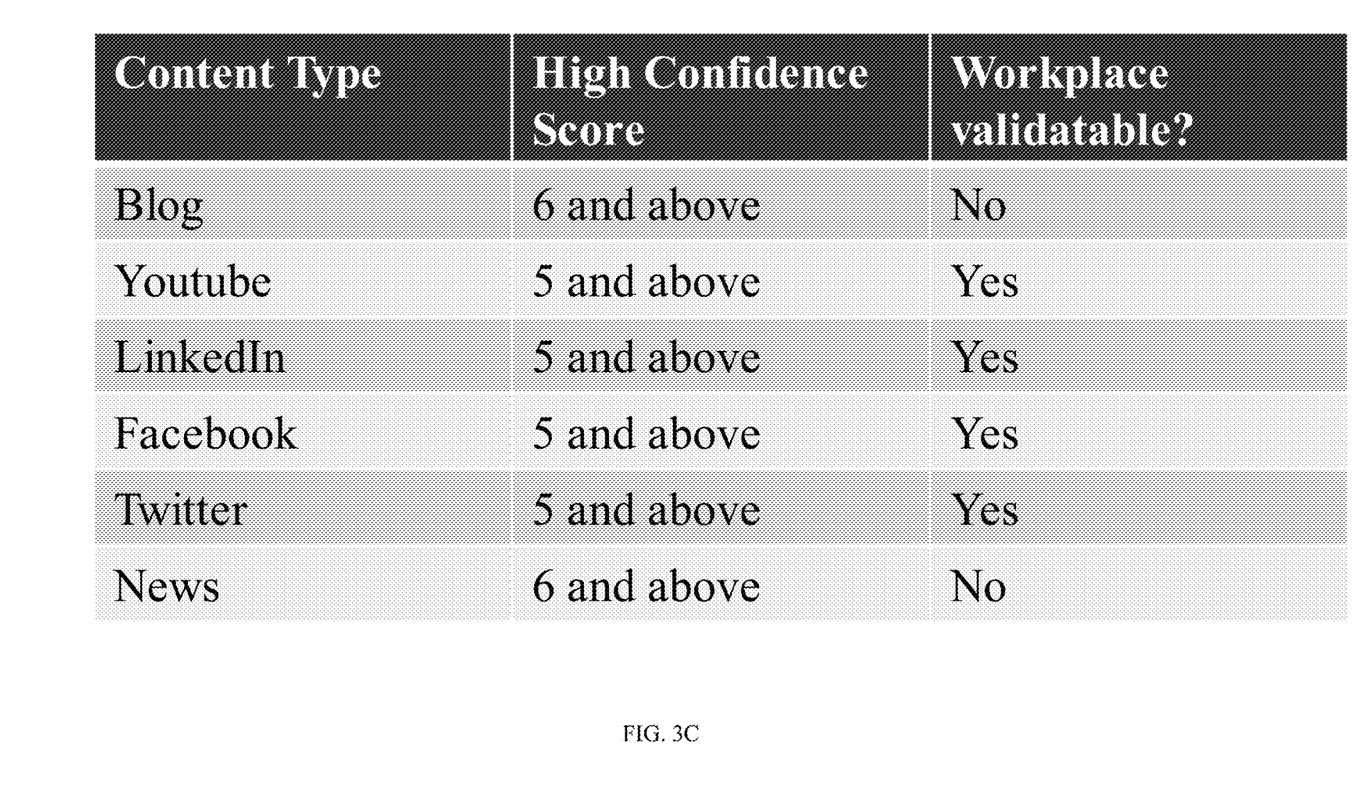
FIG. 3C shows an example authoritative index according to some implementations.

In addition to the matching index, a meta search record may be scored on an authoritative index as well. Specifically, not all social media channels are created equal. For example, professional sites like LinkedIn may include more authoritative results when a purported employment receives recommendations from coworkers or when a purported skill receives endorsements from fellow healthcare professionals. In comparison, a random tweet on tweeter may not be as reliable when the tweeted information is hard to verify or no followers can vouch for the information. Hence each social media channel may be scored differently, when targeting a particular healthcare provider. Referring to FIG. 3C, a meta search record from a blog or a news feed may need as much as six points to be deemed a high confidence score, when the workplace of the healthcare provider cannot be validated. In comparison, a meta search record from Youtube, LinkedIn, Facebook or Twitter may only need to score five points to be considered as a high confidence score, when the workplace of the healthcare professional can be validated.

Thus, in some implementations, the scoring of a meta search record may be performed according to a matching index and an authoritative index. A meta search record may be tokenized into individual tokens of the corresponding language used in posting. Tokenization may facilitate the processing of unstructured data, such as social media postings. Furthermore, in some implementations, a positive attribute, for example, a verifiable work place, in the matching index for a meta search record may even improve the authoritative index of the social medial channel where the meta search record was found.

Returning to FIG. 2, when a meta search record has been scored, filtering may be performed based on the score (210). The filtering may triage, for a vast ocean of on-line sources, the more promising leads for further consideration. The more promising leads generally may include the postings more likely to be on point. An on-point posting may be more related to the healthcare professional, a particular healthcare condition, etc.

As a result of the triage, the more promising meta search records may be provided to the user submitting the healthcare information (212). The meta search records may be provided with clickable links to the full content of the on-line posting. The human user may click on the links to follow up. For example, in some implementations, the actual contents of the postings at various social media channels may not be rated or characterized. In one configuration, the search delegators may not be configured to classify a particular on-line posting as positive or negative. Instead, the task may be reserved for the human user, who may review the full and original content of the posting, as well as the contextual information leading up to the posting. The human user may then make a subjective call, whether the content is positive or negative, whether the posting appears authentic or reliable, considering the contextual information. In another configuration, the search delegators may proactively rate or characterize the contents of the postings via machine learning or artificial intelligence, especially when coupled with user feedback. Hence, the search delegators may be constructed to be more intelligent and adaptive.

On-line data provided by a healthcare professional himself/herself may be subject to error for a number of reasons. For example, the healthcare professional may inadvertently enter a career event date (e.g., transition date from resident doctor to fellow, etc.) different from the actual career event date. Likewise, the healthcare professional may enter typos in the institution name where the healthcare professional studied or worked. The healthcare professional may also enter erroneous information about the insurance carriers that the healthcare professional may accept. The errors may or may not be intentional. However, in the context of mobile computing, more data may be entered from mobile devices in a manner less scrupulous than traditional computing devices with full-blown keyboards. All things considered, the veracity of the on-line data sources may become an issue. Even though on-line data entries may be voluminous, successful mining of the on-line data may depend on the veracity of the data entries.

Figure 4A:
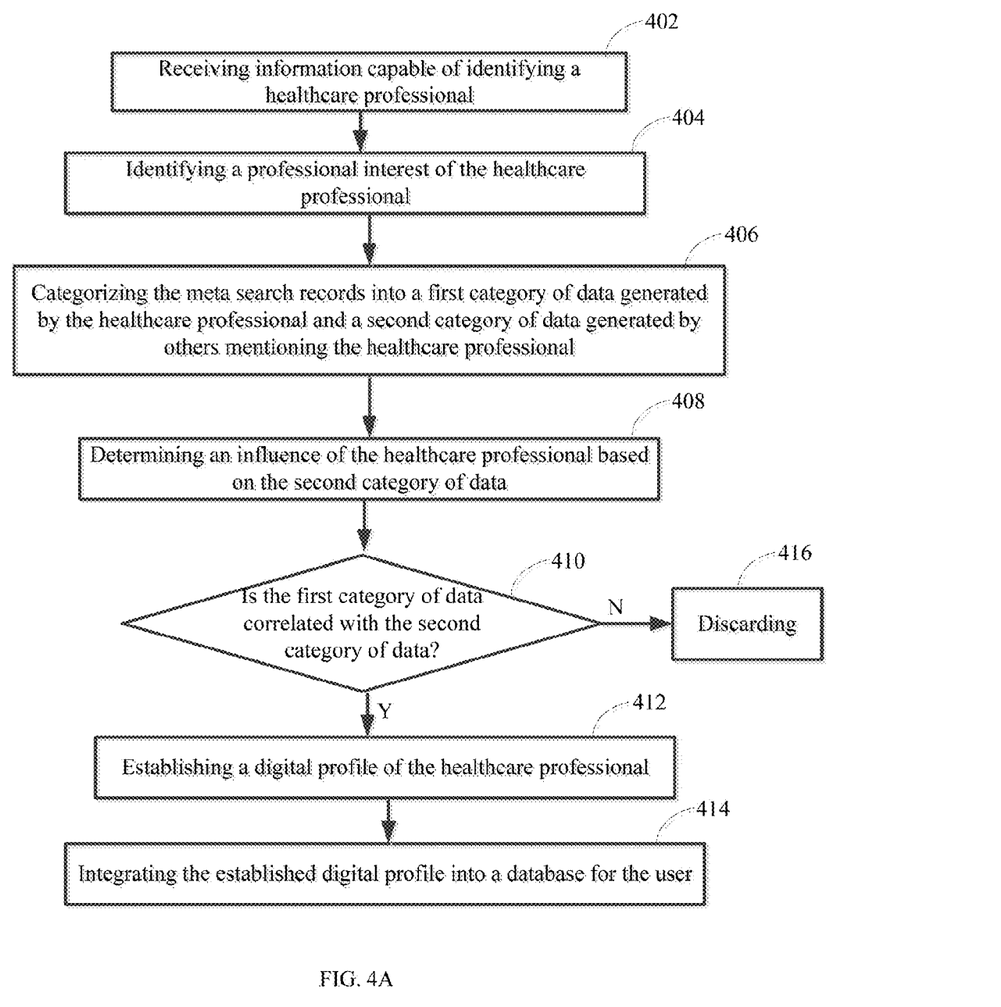
FIG. 4A is a flow chart for establishing a digital profile for a particular healthcare professional according to some implementations.

Referring to FIG. 4A, when establishing a digital profile for a healthcare professional based on social media data sources, some implementations may include a checking mechanism to automatically gauge the veracity of on-line posting. Specially, information capable of identifying a healthcare professional may be received (402). Information capable of identifying a healthcare professional may include first and last names, a specialty such as a therapeutic area, etc. In some implementations, a professional interest of the healthcare professional may be identified (404) based on, for example, self-reported specialty, the therapeutic area where the healthcare provider published predominantly (or perhaps exclusively), etc. Moreover, in some implementations, meta search records may be categorized into two categories, namely, a first category of data purportedly generated by the healthcare professional himself/herself and a second category of data purportedly generated by people other than the healthcare professional (406). For example, a healthcare professional may self-register at LinkedIn and provide information about himself/herself. Such self-registered information may fall into the first category of data generated by the healthcare professional. Conversely, fellow professionals may endorse the healthcare professional at LinkedIn, patients might provide review results at social media channels like Yelp, etc. Comments, feedback, reviews provided by on-line users other than the healthcare professional may fall into the second category of data noted above.

Digital profiles of healthcare professionals, as established, may be integrated into a database, for example, a custom-relation management (CRM) database. The database may list, for example, the top ranked healthcare professionals in a particular specialty. The database may facilitate marketing campaigns to promote a healthcare product, such as, for example, a drug, a medical device, a hygiene product, etc., through healthcare professionals who may be more likely to have an impact on others. Likewise, healthcare providers, such as health insurance companies, may utilize an integrated CRM database to provider subscribers with information on healthcare professionals for a service. The healthcare professionals may be in-network physicians, surgeons, physical therapist, etc. The healthcare professionals may also be out-of-network.

Once the meta search records have been categorized, a number of possibilities may be pursued. In one configuration, an influence of the healthcare professional may be determined based on the second category of data. The influence factor may indicate the likelihood of the healthcare professional to influence others, including fellow healthcare professionals or patients, etc. The influence factor may be based on, for example, a popularity of the healthcare professional as judged by the number of responses or followers at a social media channel (e.g., the number of followers on Twitter). The popularity may also factor in the number of publications of the healthcare professional, for example, number of blogs at a blogging site to educate fellow healthcare professional or patients. More liberally, the number of publications can include the number of speeches at professional conferences as posted by conference organizers. In particular, if the healthcare professional receives an invitation and is scheduled as an invited speaker, the healthcare professional may be treated as more likely as an opinion leader. By the same token, if the healthcare profession is scheduled to speak as a keynote speaker, for example, at a plenary session of an international conference, the healthcare professional may receive additional points for most likely to be an opinion leader. In situations in which a media file for the speech has been uploaded to social media channels like Youtube, the contents of the speech as well as feedback from the audience (either at the conference or at the social medical channel) may be analyzed (for example, through speech recognition) to further analyze how the speech was received by the community. Thereafter, the analysis may be used to augment or supplement the influence factor of the healthcare professional as determined earlier.

To determine the veracity of self-registered data, some implementations may correlate the first category of data, i.e., the data purportedly generated by the healthcare professional, with the second category of data, i.e., the data purportedly posted by people other than the healthcare professional. The correlation may seek to confirm the self-registered data as entered by the healthcare professional. For example, if the particular healthcare professional claims to have worked at an institution, the confirmation may come from recommendations from fellow healthcare professionals who worked at the institution during the same period of time. Fellow healthcare professionals other than the particular healthcare professional, i.e., coworkers, may vouch for the veracity of the self-registered data by recommending the subject's service or endorsing the subject's skill. The recommended service may be rendered during the subject's tenure at the institution. The endorsed skill may be acquired by the subject during the purported service period at the institution. Although not a fail-safe approach, former coworkers generally have no incentive to collude with the particular healthcare professional to fabricate a story. Therefore, if the first category of data is correlatable with the second category of data, the correlation may serve as prima facie support for the veracity of the first category of data. If the correlation exists, then a digital profile of the particular healthcare professional may be established (412). The digital profile may be based on the first category of data correlatable with the second category of data. The digital profile of the particular healthcare professional may then be integrated into a database for the user who initially submitted healthcare information 102 (414).

On the other hand, if the first category of data is not correlatable with the second category of data, for example, when the self-registered data contradicts with comments purportedly made by fellow healthcare professionals, the uncorrelatable portion of self-registered data may be discarded (416). Some implementations may favor a presumption of veracity and may treat self-registered data as authentic unless contrarian reports are available. Other implementations, may favor a rigorous presumption of invalidity unless the self-registered data can be confirmed by comments made by fellow healthcare professionals.

Figure 4B:
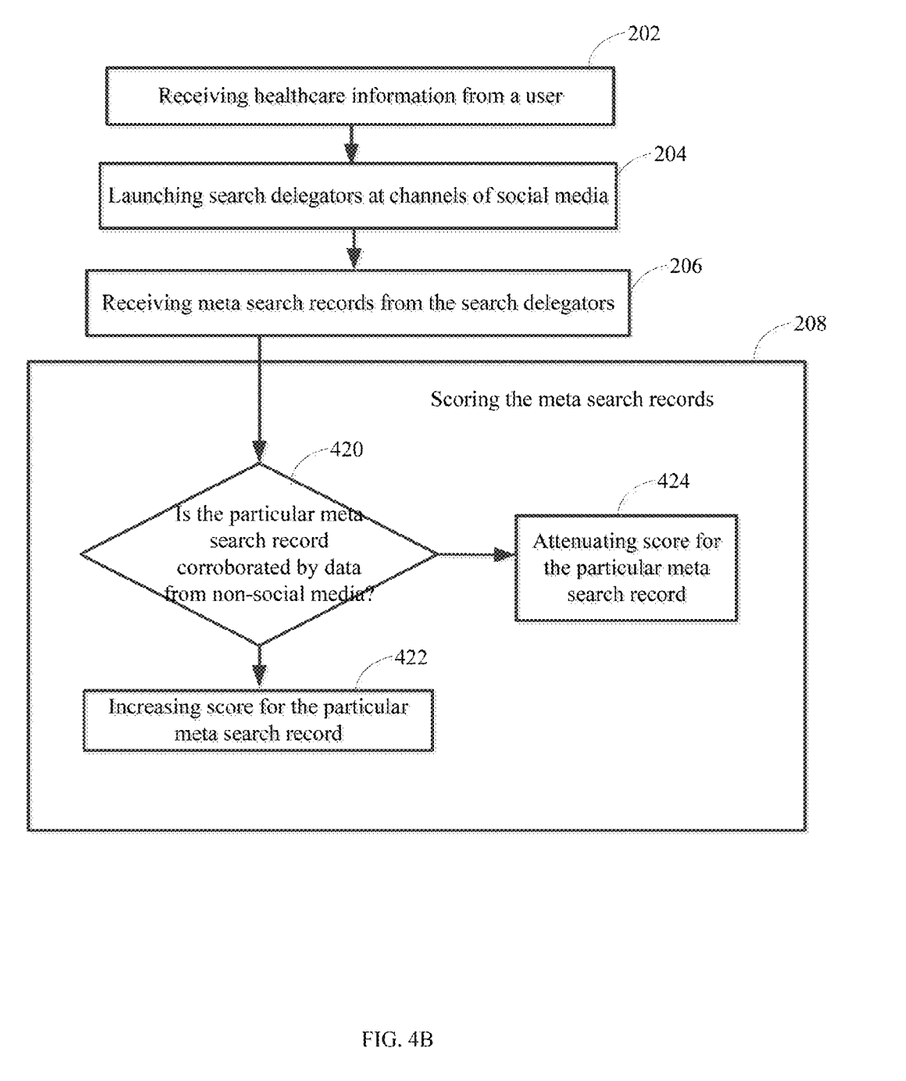
FIG. 4B is a flow chart for adjusting score for an identified search record for a particular healthcare professional according to some implementations.

In addition to relying on comments from other healthcare professionals, some implementations may correlate a particular meta search record with more traditional data sources, such as directory of an institution, yellow pages, academic publications, etc. Referring to FIG. 4B, showing a flow chart for adjusting score for an identified search record for a particular healthcare professional, healthcare information may be received from a user (202). In response, search delegators may be launched (204), for example, as web-crawlers or spiders. Thereafter, meta search records may be received from the search delegators (206).

During scoring of the received meta search records (208), more traditional sources may be consulted. Specifically, some implementations may seek to corroborate the meta search record with data from non-social media channels (420). Non-social media channels may include academic publications (e.g., journal publications as achieved by national library of medicine or Library of Congress), clinical trial record (e.g., as registered at Federal Drug Administration or the Center for Disease Control). For self-registered data by the subject healthcare provider, for example, purported employment at a hospital, the employment history may be corroborated by author affiliations of academic papers published or submitted during the purported tenure at the hospital. As the academic papers were peer reviewed, the inherence correspondence back and forth between the publishing journal and the author may function as collateral proof that the subject healthcare professional worked at the hospital during the review period. Likewise, academic publications may function as collateral proof that fellow healthcare professionals, who commented on postings by the subject healthcare professional, were in the same or similar therapeutic area and were qualified to make substantive comments. If the particular meta search record can be corroborated by data from non-social media sources, then the score for the particular meta search record may be increased (422). On the other hand, if the particular meta search record is not corroborable, then the score for the particular meta search record may be attenuated. For example, when the author was affiliated with an institution different from the one purported by the subject healthcare professional for the period of time that includes the submission and publication dates of the academic paper, the discrepancy may amount to a contradiction, in the absence alternative spellings or hospital merge events. The discrepancy may be particularly alarming if, for example, the purported address differs from the author's address. Thus, even though social media postings are uncensored, the veracity of the contents may still be verified to some extent by correlation or corroboration mechanisms as disclosed herein.

Figure 5:
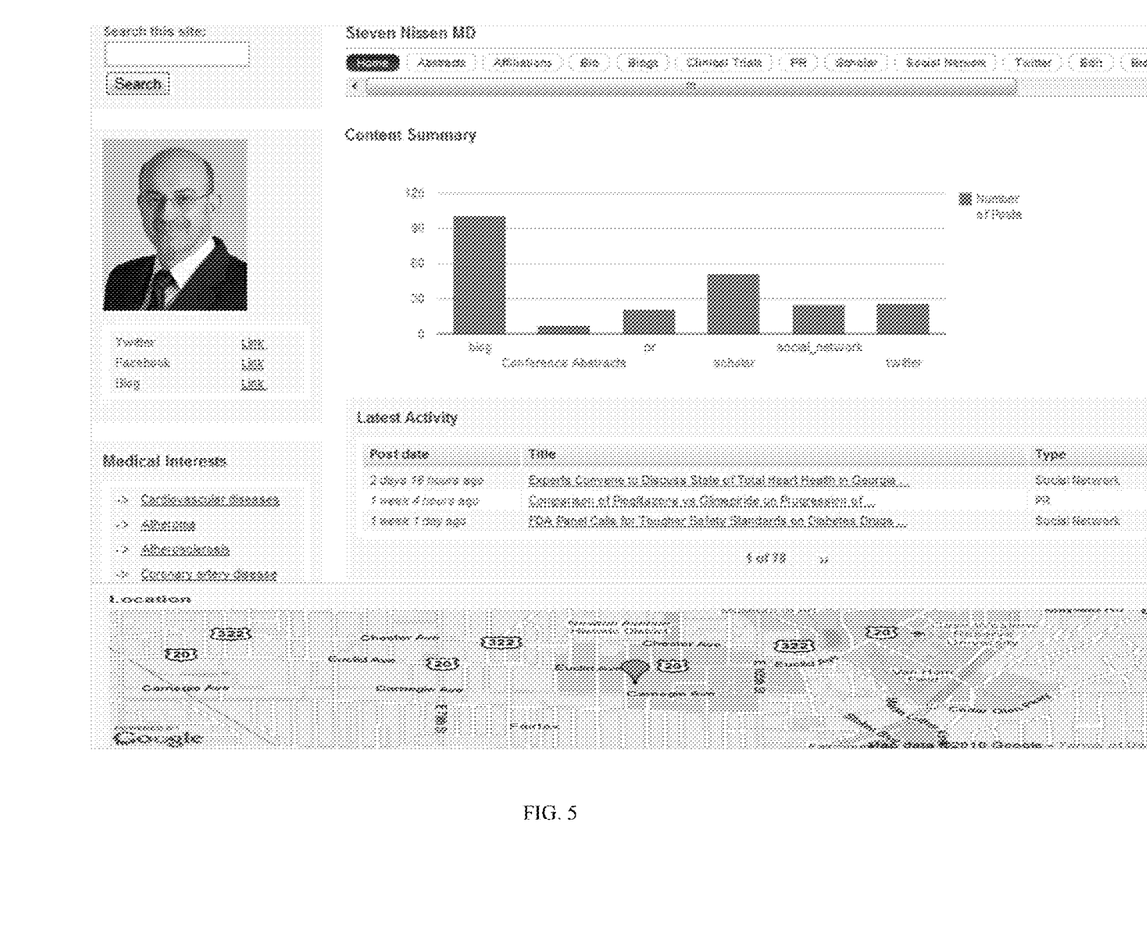
FIG. 5 shows an example user interface for a user to review the identified meta search record for a particular healthcare professional.

Implementations according to the discussions herein may provide intuitive results to a user. FIG. 5 shows an example user interface for a user to review the identified meta search record for a particular healthcare professional. As illustrated, a leading cardiologist has been identified. Links to his twitter, Facebook, and Blogs are available. In accordance with the disclosures herein, his professional interests have been identified to include cardiovascular diseases, atheroma, atherosclerosis, coronary artery disease, etc. The quantity of his blogs, conference abstracts, news reports, scholastic publications, social network postings, and twitter mentions are tabulated. His latest activities have also been identified and listed. In addition, a map of his professional location, i.e., the hospital where he works, is also presented.

Implementations discussed herein may allow a system administrator to configure a particular semantic attribute used to rank meta search records. The system administrator may configure the semantic attributes for ranking meta search records from within the source code, a configuration file, or via a user interface.

In a similar vein, other service professionals may be scored or ranked in a manner consistent with the description herein. For example, contractors (for roof replacement, kitchen or bathroom remodeling, etc.), lawyers (for person injury, employment related injury, etc.), personal trainers (for fitness, bodybuilding, sports, etc.) may be scored and ranked according to data on social media channels referring to their service. Data on social media channels may be posted by the professionals themselves or others who have worked with the professional or have received service from the professional.

Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combinations.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

The invention claimed is:

1. A computer-implemented method for ranking healthcare professionals, comprising:
   receiving, by a search engine, healthcare information submitted by a user;
   launching, by the search engine, search delegators to search respective channels of social media based on the healthcare information;
   receiving, by the search engine, meta search records from the search delegators;
   scoring, by the search engine, the meta search records based on the healthcare information as well as the channel of social media where the meta search record was found by ranking the meta search records according to (i) a match index indicating a degree of relatedness between each search record and the submitted healthcare information, and (ii) an authoritative index indicating an authority level of the channel of social media where the particular search record was found by the corresponding search delegator; and
   filtering, by the search engine, the meta search records based on the corresponding scores such that the filtered meta search records are automatically provided to the user based on the corresponding scores.

2. The method of claim 1, wherein ranking the meta search records according to the match index further comprises: semantic processing of the meta search records by: (i) tokenizing the particular meta search records into tokens; (ii) scoring each token based on the match index; and (iii) aggregating scores of the tokens for the particular meta search record.

3. The method of claim 2, wherein the semantic processing comprises: applying an ontology to analyze the meta search records.

4. The method of claim 3, wherein the semantic processing further comprises: revising the ontology based on the analyzed meta search records, the revised ontology providing an improved aggregated score for the analyzed meta search records.

5. The method of claim 1, wherein filtering further comprises: removing meta records with corresponding scores under a cut-off threshold.

6. The method of claim 1, further comprising:
providing an interface to the user for the user to classify contents of the filtered meta data records as positive, negative or neutral.

7. The method of claim 1, wherein receiving healthcare information comprises: receiving information capable of identifying a healthcare provider.

8. The method of claim 7, wherein receiving healthcare information comprises: receiving information identifying a specialty of healthcare providers.

9. The method of claim 7, wherein scoring the meta search records comprises categorizing the meta search records into a first category of data generated by the healthcare provider and a second category of data generated by others mentioning the healthcare provider.

10. The method of claim 9, wherein scoring the meta search records further comprises: identifying a professional interest of the healthcare provider based on the first category of data.

11. The method of claim 10, wherein scoring the meta search records comprises analyzing the second category of data to determine whether the first category of data is correlated with the second category of data.

12. The method of claim 11, further comprising:
in response to determining that the first category of data is correlated with the second category of data, establishing a digital profile of the healthcare provider based on (i) the identified professional interest of the healthcare provider; and (ii) the first category of data of the healthcare provider correlated with the second category of data of the healthcare provider; and
integrating the digital profile into a database for the user that includes digital profiles of more than one healthcare providers.

13. The method of claim 10, wherein scoring the meta search records comprises analyzing the second category of data to determine an influence of the healthcare provider.

14. The method of claim 13, further comprising:
establishing a digital profile of the healthcare provider based on (i) the identified professional interest of the healthcare provider; and (ii) the influence of the healthcare provide as determined by analyzing the second category of data of the healthcare provider; and
integrating the digital profile into a database for the user that includes digital profiles of more than one healthcare providers.

15. The method of claim 7, wherein scoring the meta search records further comprises:
determining whether a particular meta search record is corroborated by data from non-social media regarding the healthcare provider.

16. The method of claim 15, wherein scoring the meta search records further comprises:
in response to determining that the particular meta search record is corroborated by data from non-social media, increasing the score of the particular meta search record.

17. The method of claim 16, wherein scoring the meta search records further comprises:
in response to determining that the particular search record is not corroborated by data from non-social media, attenuating the score for the particular search record.

18. A computer system, comprising at least one processor, wherein the at least one processor is configured to perform the operations of:
receiving healthcare information submitted by a user;
launching search delegators to search respective channels of social media in response to the healthcare information;
receiving meta search records from the search delegators;
scoring the meta search records based on the healthcare information as well as the channel of social media where the meta search record was found by ranking the meta search records according to (i) a match index indicating a degree of relatedness between each search record and the submitted healthcare information, and (ii) an authoritative index indicating an authority level of the channel of social media where the particular search record was found by the corresponding search delegator; and
filtering the meta search records based on the corresponding scores such that the filtered meta search records are automatically provided to the user based on the corresponding scores.

19. A computer-readable medium comprising software instructions that, when executed by a computer, causes the computer to perform the operations of:
receiving healthcare information submitted by a user;
launching search delegators to search respective channels of social media in response to the healthcare information;
receiving meta search records from the search delegators;
scoring the meta search records based on the healthcare information as well as the channel of social media where the meta search record was found by ranking the meta search records according to (i) a match index indicating a degree of relatedness between each search record and the submitted healthcare information, and (ii) an authoritative index indicating an authority level of the channel of social media where the particular search record was found by the corresponding search delegator; and
filtering the meta search records based on the corresponding scores such that the filtered meta search records are automatically provided to the user based on the corresponding scores.

* * * * *